United States Patent [19]

Feldstein

[11] Patent Number: 4,795,429
[45] Date of Patent: Jan. 3, 1989

[54] METHOD AND APPARATUS FOR USE IN THE CONTROL OF INTRAVENOUS MEDICATION INTRODUCTION

[76] Inventor: Marvin A. Feldstein, 10235 Wisner Rd., Kirtland, Ohio 44094

[21] Appl. No.: 114,243

[22] Filed: Oct. 28, 1987

[51] Int. Cl.$^4$ .............................................. A61M 5/14
[52] U.S. Cl. ........................................ 604/80; 604/82; 604/86; 604/174; 128/DIG. 26
[58] Field of Search ....................... 604/80, 82, 83, 85, 604/86, 174; 128/DIG. 26

[56] References Cited

U.S. PATENT DOCUMENTS

| | | | |
|---|---|---|---|
| 2,954,028 | 9/1960 | Smith | 604/80 |
| 3,210,816 | 10/1965 | Clemons | 604/174 |
| 3,696,920 | 10/1972 | Lahay | 128/DIG. 26 |
| 4,121,585 | 10/1978 | Becker, Jr. | 604/86 |
| 4,534,762 | 8/1985 | Heyer | 128/DIG. 26 X |
| 4,625,494 | 12/1986 | Iwatschenko | 604/82 X |

FOREIGN PATENT DOCUMENTS

1471609  4/1977  United Kingdom ....... 128/DIG. 26

*Primary Examiner*—Allen M. Ostrager
*Attorney, Agent, or Firm*—Donald A. Teare

[57] ABSTRACT

A method and apparatus for increasing the accuracy of administration of intravenous medicinal fluids including an elongated matrix device attachable to a plurality of intravenous tubes, so that each tube is disposed in spatial and visual alignment with an indicia device on which the type of fluid flowing in the tube and the identification of the body port to which the fluid is flowing is recorded, as well as visual means, such as staggered positioning, is used to visually connect the tubes coming into the matrix with the corresponding effluent tube to a particular body portal, and including the use of color coding as an enhancement to the basic arrangement.

19 Claims, 5 Drawing Sheets

METHOD AND APPARATUS FOR USE IN THE CONTROL OF INTRAVENOUS MEDICATION INTRODUCTION

BACKGROUND OF THE INVENTION

1. Field of the Invention

The present invention relates to an apparatus and system for use in connection with intravenous fluid devices, and more particularly to a method, system and apparatus for increasing the accuracy of adding to or changing the intravenous fluid flow to a patient in hospitals, clinics, and other medical institutions.

2. Discussion of the Prior Art

The treatment of patient often requires the simultaneous administration of several intravenous solutions, and/or the use of intravenous catheters and monitoring devices for such measurements as central venous pressure, pulmonary artery and pulmonary wedge pressures. These solutions and catheters are routinely utilized following cardiac and pulmonary surgery or other major surgical procedures, in the treatment of shock or severe sepsis, and in the care of myocardial infarcts associated with major complications.

In order to administer these intravenous fluids and medicines, while at the same time monitoring various cardiopulmonary functions, multiple sites for introduction of the fluids are provided on the patient. For example, a subclavian vein catheter with multiple ports is commonly inserted above the clavicle and lateral to the neck into the subclavian vein, a single port catheter or needle is placed in a vein in the forearm, and often a third venous catheter or needle is used elsewhere on the forearm or hand. Four or more containers, more often plastic bags, containing intravenous fluids, often are suspended around the critically ill patient. Some of these are administered continuously, while others are used intermittently. The transport of the fluid from these containers to the patient is accomplished through the means of small gauge clear plastic tubes which are connected to a variety of needles and/or catheters inserted into the patient. The flow is either directly through these tubes or through intermediate mechanical pumps or measuring devices to more accurately adjust the flow rate of fluids.

However, the number of fluid containers usually exceeds the number of intravenous portals into the patient. A common way of overcoming the problem is to place a flow control means such as two and three way stopcocks interposed in the intravenous lines, with two or more bottle effluent lines flowing into the stopcocks and one line flowing out towards the patient, and/or with an intravenous line flowing into a rubber tipped side port from which one line flows out to the patient. This latter method is often referred to as a "piggyback" method. These side ports are found on most intravenous tubing for this purpose. Such "Y"s fulfill another very important purpose in emergency situations where it is necessary to administer medication to the patient immediately. When this occurs, a needled syringe is inserted into the stoppered appendage and medication is injected directly through the side port and through the output tubing into the vein of the patient. This method is routinely used in administering drugs, especially to the critically ill patient or to one who is unable to take oral medication.

Not only must the correct medication be introduced into the patient, but it is also extremely important that the medication be entered into the proper portion of the patient's body. For example, a patient might have intravenous input ports in the arms or hands, which input medication into the peripheral system, and other ports in the upper body which lead to the subclavian vein or past the heart into the pulmonary artery without passing through the peripheral system. The difference is important. Most direct intravenously administered drugs should be introduced into the peripheral circulation for a dilutional effect before entering the heart and lungs. Some drugs are potentially dangerous if injected directly in the heart chambers or the pulmonary artery. As a result, the nurse must be careful to select the proper port for the injection. In addition, if the medication from one container is to be combined in introduction with medication from another container it is important that the containers be properly selected so that a deleterious or dangerous combination does not occur.

But there exists the potential of making a mistake in selecting the tubing which leads to the proper port, as well as in selecting the tubing already carrying medication with which the new medication is to be combined. The patient is usually surrounded by a bewildering array of intravenous containers, mechanical pumps, and intravenous tubing, with the latter traversing the bed like spaghetti before finding its way either directly into the patient or through a needle into another line or perhaps through a stopcock into another tube and into the patient. The bottles are remote from the patient, the lines are tangled, and it is difficult to be certain that the newly administered, continued, or changed medication is going into the proper body port. When containers become empty, when intravenous tubing needs to be replaced, and especially when direct intravenous medication is required, the nurse must carefully search out the origin and insertion of a specific bottle or line, confirm that the line is operable, and be certain that the drug be administered into the proper intravenous portal. The procedure is time consuming and sometimes frustrating, and in an emergency situation, such as cardiac arrest, the delay can be deleterious to the patient. Moreover, if the wrong port is chosen, due to the confusion resulting from the tangling misalignment it can be extremely dangerous and sometimes even fatal. In addition to the ordinary tendency for confusion and error, the matter is exacerbated during the transportation of the patient to a stretcher or wheelchair, or in turning the patient or making up the bed when the complex of lines tend to become twisted or pulled. The problem is still further complicated by the fact that the new or additional medication is not inserted directly at the portal to the body, but rather at a more removed portion on the tubing length which leads from the portal where the "Y", or other connectors or valves are located. Because such connectors and valves are located remotely from the body portals and from the containers the confusion resulting from the maze of lines is increased, particularly where the personnel involved are fatigued or rushed. What is needed is a method of accurately determining, often under conditions of urgency and stress, and sometimes of fatigue, what fluid is flowing in a particular line, and what is the body port to which what medication is flowing, despite the entangling complexity of tubing, the shifting position of bottles relative to the patient, and the constant changing of the medicinal requirements, and without having to commit to memory something like a color code.

Therefore, an object of the present invention is to provide a system and apparatus for permitting rapid and accurate identification of the fluid flowing through IV tubing in the area of the Y-Connector, or other connector or valve where new fluid is to be inserted into the tubing.

Another object is to provide a system where cross checking to be sure the new or additional IV fluid is inserted in the correct tubing is prompted, encouraged and facilitated, yet where the total installation time is not adversely affected or wherein the installation is too complicated or made a chore which the nurse may want to avoid or circumvent.

An additional object is to provide a system which is easy to learn, and which employs habits already ingrained in the nursing profession so as to enhance its use.

Another object is to provide a device which can readily be integrated into an effective system, and yet which is inexpensive so that it can be readily replaced to maintain the cleanliness and enhance the sterility of the environment in which it is used.

An additional object is to provide a system which can accomodate the constantly changing circumstances and nature of administration of medication to a patient over the time period that the patient is in need of intravenous introduction of medication.

A still further object is to provide a system which not only provides for correct installation, but provides a temporary or permanent record of the fluid which was admininstered over a period of time.

SUMMARY OF THE INVENTION

Briefly, the above and further objects of the present invention are realized in accordance with the present invention by providing a lightweight, inexpensive visual control device which can be readily attached to an array of tubing adjacent the fluid flow junctures, such as Y or other connectors, where new medication is injected into the system, whereby an independent attachable means is provided for recording by a visual alignment technique flow controlling information to accurately direct the newly added fluid into the correct tubing, so that the nurse can readily and precisely determine that the new medication is being inserted into the correct tubing, and where a permanent record of the medication which was used is automatically maintained in carrying out the system. This is particularly important in the contemporary hospital or clinic environment where it has become increasingly necessary to provide accurate records of how and where medication is administered.

In one form of the invention, the visual coordination means includes color alignment means which is established by, coacts with and is controlled by the recording means.

By the present invention a novel system is provided for enhancing the accuracy of administration of medication, in a manner that is easy to learn, rapid to use, and which provides a crosscheck at the time of application, and simultaneously a permanent contemporary record.

BRIEF DESCRIPTION OF THE DRAWINGS

FIG. 7A is an enlarged fragmentary view of the writing platform of FIG. 6, showing the first four tapes filed in.

Figure 1:
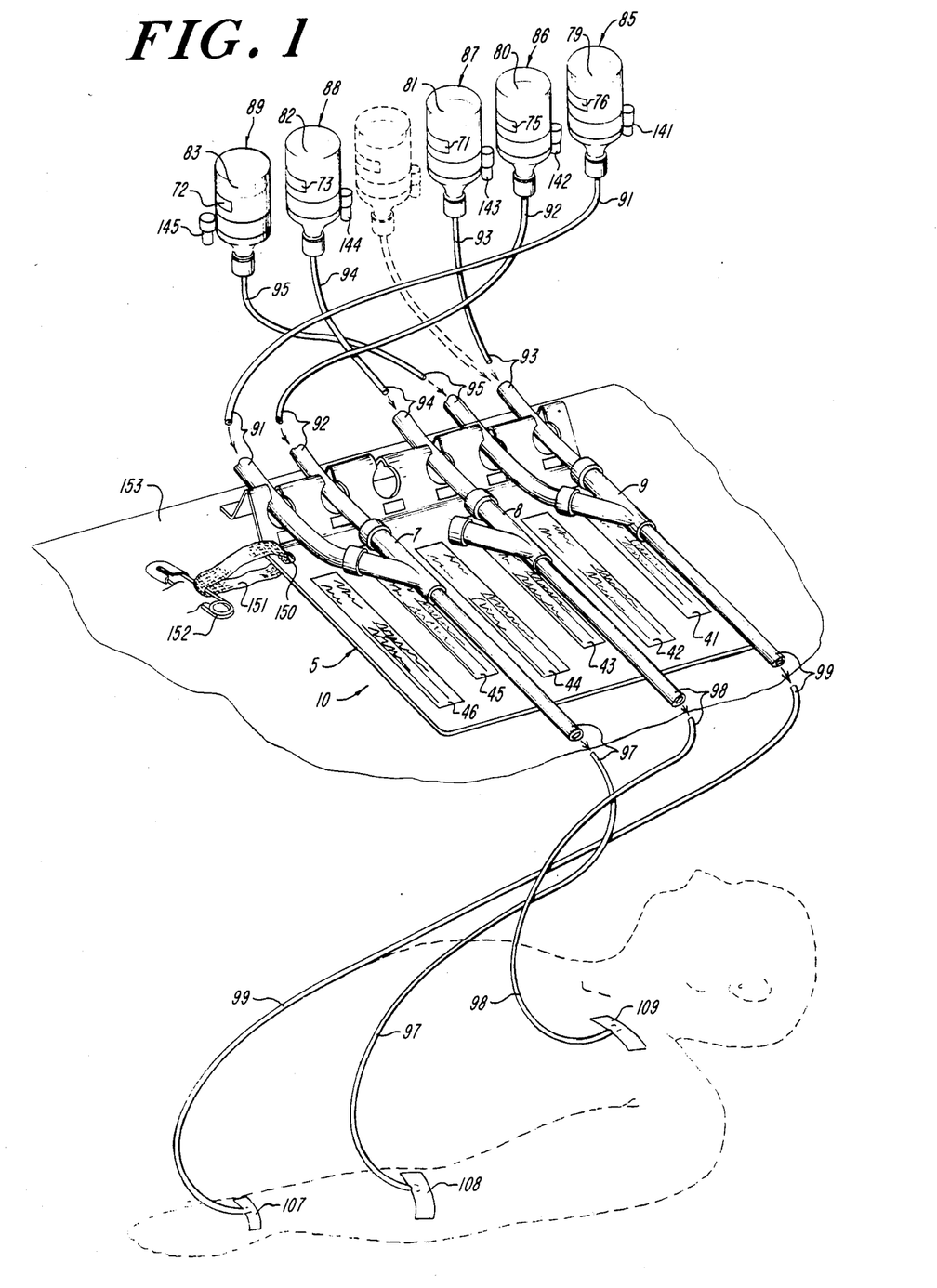
FIG. 1 is a perspective view of the system and fluid flow control matrix device of the invention installed on a plurality of intravenous tubes adjacent the fluid flow junctures formed by a plurality of Y connectors, with the matrix and its immediate connectors enlarged.

Referring again to the drawings, FIG. 1 shows an example of an intravenous fluid hook-up, with the device of the present invention already in place. For clarity, the portion of the system which comprises the matrix device and its immediate connections is enlarged. A plurality of intravenous fluids, such as five fluids 79–83 from five bottles 85–89 mounted on stands 141–145 have flow paths through five bottle effluent tubes 91–95, past the matrix device 10 of the present invention, and into two "y" connections 7, and 9 and a rubber stoppered side port 8 where the flow paths are combined into fewer tubes, such as the three patient connecting tubes 97–99 which are connected to a patient 4 through hand portal 107, forearm portal 108, and clavical portal 109 respectively. In accordance with the present invention, the matrix device 10 provides for the accurate connection of the tubing to the Y connections so that the appropriate fluid is caused to flow to the correct body portal as changes are repeatedly made in the fluid input, in spite of the maze of tubing and the confusion inherently present in the addition of the new fluids.

Figure 2:
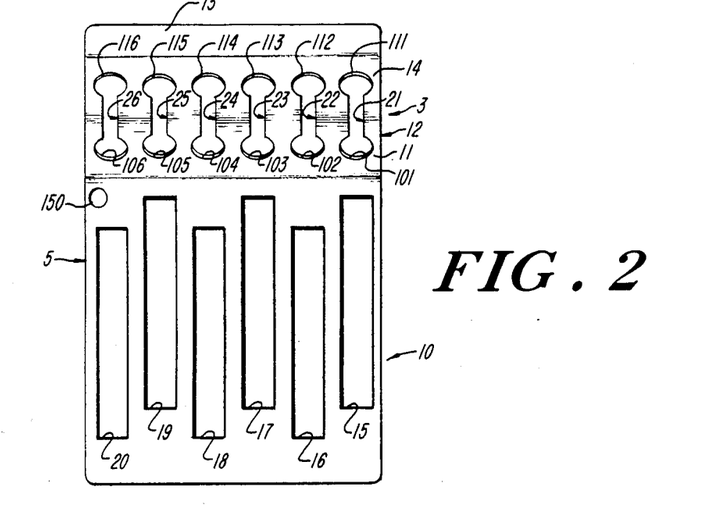
FIG. 2 is a perspective view of a partial assembly of one form of matrix device wherein the recording means includes recess means;.
Figure 3:
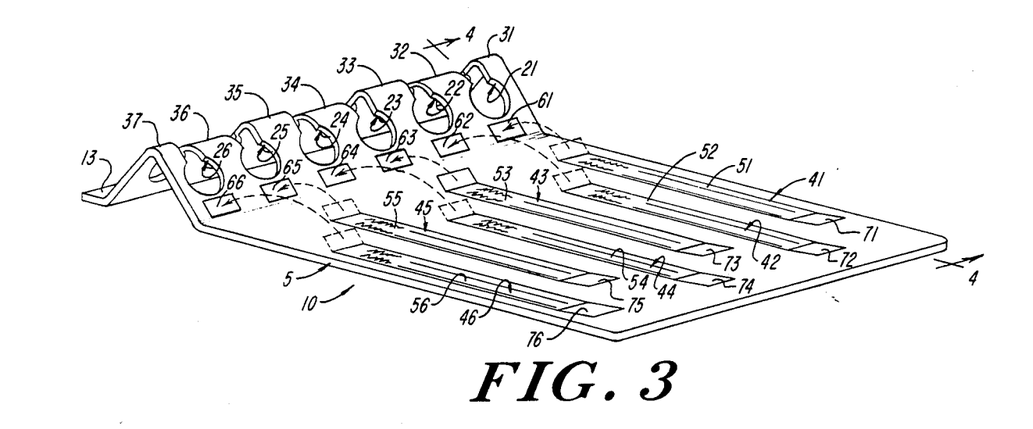
FIG. 3 is a perspective view of the device of FIG. 2 with one form of tape means installed in the recording means.

As shown in FIG. 2, the matrix device 10 has at one end a tube aligning means, such as a slotted upright flange or corrugation 3, having a plurality of spaced tube holding means such as slots 21 to 26 to hold bottle effluent tubes in a particular alignment relative to a recording means in the form of a long platform 5, on which notations can be made in visual alignment and correlation with corresponding portions of the tube aligning means 3, in accordance with the present invention, as more fully explained hereinafter. In the preferred embodiment, as shown in FIG. 3, such visual correlation, as well as other additional advantages, is preferably enhanced by the tops of the webs 31–37 which form the leading edges of the slots 21–26 on the tube aligning means 3 being staggered and the tape holding recesses 15–20 (FIG. 2) being correspondingly staggered so that the fluid tubes and their corresponding aligned tapes 41 to 46 (FIG. 3) which are placed in the recesses 15–20 are visually disposed in pairs which will lead to a common patient portal. In a preferred embodiment, color alignment means 61–66 of the same color as the tape means 41–46 are removed from the tape means and placed on the tube holding means below each corresponding tube holding slot 21–26 to further assist in the visual alignment of the tubing with the written recorded data on the tape means 41–46. In a further modification, each tape means also has a removable color indicia means such as tabs 71 to 75 adapted to be removed and placed on the bottles such as 85–89 for providing additional visual correlation between the fluid recorded on the matrix device and the fluid contained in the bottles so as to provide an additional cross check.

Figure 4:
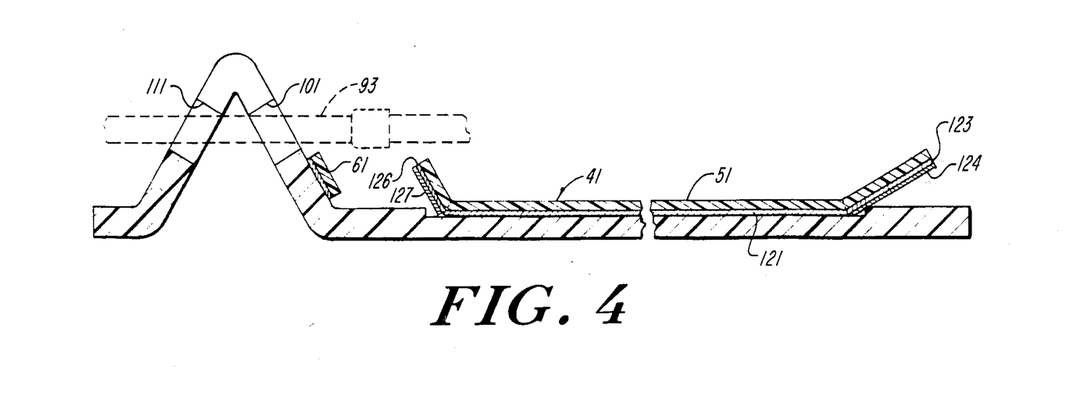
FIG. 4 is a vertical cross sectional view of the assembly of FIG. 3 taken along the lines 4—4 in FIG. 3.

One form of matrix device in accordance with the present invention is shown in FIG. 2. The device is made of a lightweight plastic material such as ABS, and of unitary molded construction. Tube aligning means 3 is provided in the form of a corrugation or v-shaped upright flange portion 12 having a front side 11 and a rear side 14, with a plurality of paired slots such as slots 21 to 26. As seen better in FIG. 3, the slots are visually divided into pairs by the web portions 31–37 being of staggered heights so that pair members are disposed to either side of a shorter web. Thus slots 21–22 separated by short web 32 form a first pair, slots 23–24 separated by short web 34 form a second pair, and slots 25–26 separated by short web 36 form a third pair. Turning again to FIG. 2, the slots terminate in eye portions 101 to 106 on the front side 11 of the flange, and eye portions 111 to 116 on the back side 14 to provide the means for attaching the matrix to the tubing in a manner to provide a desired visual spatial orientation of the tubing relative to the recording means. The slots 21 to 26 are slightly narrower than the tubes 91 to 96 which the slots are adapted to receive,(FIG. 1) and the eye portions 101 to 106 and 111 to 116, (FIG. 2) are slightly larger than the tubing, so that the tubing slides through the slots in a slightly compressed state and then expands into the eye portions whereby it is held by slight frictional engagement. An example of such arrangement is shown in FIG. 4 by tubing 93 (in phantom) disposed in eyes 101 and 111. For ease of manufacture, and additional stability in the writing operation, the corrugation terminates in a horizontal flange 13.

The matrix device 10 is provided with a long writing platform 5 for recording in visual alignment with each tube attached to the tube holding means the fluid flowing in and the body portal destination of each such tube. It is preferred that such platform be at least two inches long to provide adequate space for writing. In the preferred embodiment of FIG. 2, guide means are provided on the platform 5, to assist in the visual alignment of the writing. In the embodiment of FIG. 2, the guide means are in the form of a plurality of rectangular recesses 15 to 20, which, in conjunction with the tape means described hereinafter, provide a preferred guide means and method for the recording of the data in visual alignment with the tube positioned in the appropriate slot. Each of the recesses 15–20 is of a sufficient width, length, and depth to accomodate the writing tapes 41–46, (FIG. 3) as well as to permit easy insertion of the tapes, their retention during use, and their ease of removal when the tapes are removed for placement on the back of the device for storage.

It is preferred that visual means be provided for grouping the tubes in pairs corresponding to a common patient portal, and to provide a visual guide as to which tube of the pair should be entered first. To accomplish this objective, the tube holding slots 21–26 are visually grouped in pairs, by the webs 31–37 of the upward flange 12 of the tube holding means 3 being staggered for ready visual identification of the slots as pairs. Similarly, as shown in FIGS. 2 and 3, the recesses 15–20 in the writing platform 5 are also staggered, with each pair having one recess nearer its tube holding slot than is the recess of its adjacent pair. As a result, the leading slot of each pair appears to be "higher" than the adjacent slot of its pair, just the same as the leading slot forming web, such as web 31, is higher than the adjacent slot forming web 32 (FIG. 3). Thus, not only are the slots and recording means aligned in pairs, but the leading slot is visually indicated as the first slot of a pair into which the tube should be entered. For example, recesses 15 and 16 form a pair, with recess 15 being nearer its aligned tube holding slot 21 than recess 16 is to its aligned tube holding slot 22. Recesses 17 and 18 provide a similar visual arrangement for tube holding slots 23 and 24, and recesses 19 and 20 do the same for tube holding slots 25 and 26. By this arrangement, a visual connection between the slot pairs and the tapes can readily be established. In addition, the nearer tape can always be a guide as to which slot of a pair should first receive a tube.

As shown in FIG. 3, a plurality of slot aligned tapes 4146 provide the preferred means for providing the novel recording in accordance with the system of the present invention. In the preferred form, the tapes are made of a strong material upon which writing can be made, by pen or pencil. The body portions of the tapes, such as body portion 51 shown in FIG. 5A, are printed in a first column to provide for the identification of a fluid, such as the legend, "Fluid", as shown at 51A, and the identification of the patient port, such as the legend, "Portal", as shown at 51B. Lines, such as blank lines 51C and 51D are then provided as extensions of legends 51A and 51B respectively and, accordingly parallel to the lengthwise sides of the body 51 so that all of the notations are in visual alignment with, and a continuation of a corresponding tube aligning slot, in this case, slot 21 for tape 41. The aforesaid lines 51C and 51D are thus positioned so that when they are filled in by the nurse in a manner to be described hereinafter, they are positioned so as to function as a key part of the system.

As shown in FIG. 4, the body portion of each tape has an adhesive layer such as layer 121 on the body portion 51 of tape 41. The tape may be the kind that comes on a roll and has an adhesive that is not pressure sensitive to the top portion of the tape, but is pressure sensitive to the material of the writing platform 5, or it can be installed by the use of a release sheet (not shown). In any event, in the preferred embodiment, it is preferred that the tapes be preinstalled on the matrix device at the point of manufacture.

As an additional means to enhance and reinforce the already established connection and visual alignment between such data to be recorded on the blank lines C and D of tape bodies 5156 and their corresponding aligned tube holding slot, each tape body such as 51 to 56 has a color visual alignment assistance means, such as each tape body 51-56 being a different color.

In the preferred embodiment, each tape body 51-56 has a removable color alignment tab 61-66 disposed at one end. The tab is the same color as the tape body to which it is originally attached. Each tab 61-66 has a pressure sensitive adhesive layer and a release paper, such as is shown at 126 and 127 respectively (FIG. 4) for the tab of tape body 51. When the release papers are removed, and tabs 11-66 are placed on the tube alignment means 3 below their respective slots 21-26, an additional visual correlation is provided between the identification of the fluid and portal and the tubing to which this identification applies.

In addition, in accordance with one embodiment, as a further cross-check, the tapes may have additional tear portions such as 71-76 which are of the same color as the body of the tape. Each of these tabs has an adhesive layer, such as adhesive layer 123 for tab 71 of tape body 51, and a release paper, such as release paper 124 for adhesive layer 123. These tabs can be removed and placed on the bottles of the effluent as each corresponding effluent tube is installed, as a further cross check, both by the nurse making the installation, and later by a supervising nurse.

As shown in FIG. 1, a hole, 150 in the upper corner of the matrix provides for the attachment of the device, if desired, to the bed sheets, such as by gauze or rubber bands placed through the hole and pinned to the bed covering as shown by gauze 151, and pin 152 which hold the device to the bedsheet 153. Such loose attachment allows movement of the matrix, as the purpose is no to provide a fixed securement, but rather merely a proper identification.

It is to be understood that each bottle effluent tube and patient connecting tube would have one or more slide clamps and/or roller clamps (not shown) for shutting off the flow in the tubing when desired.

FIGS. 3 and 5-7 illustrate the preferred method of using the preferred embodiment of the invention. At the start, (FIG. 3) it is preferred that all of the tapes, such as 41 to 46 be in place on the platform 5 of the matrix device, and that the color aligning tabs 61-66 be in place below the slots 21-26. As shown in FIG. 3, at the start there is no hand writing on the tapes. Only the preprinted matter, "Fluid ", and "Port", and the blank line extensions thereof, appear thereon.

Figure 5:
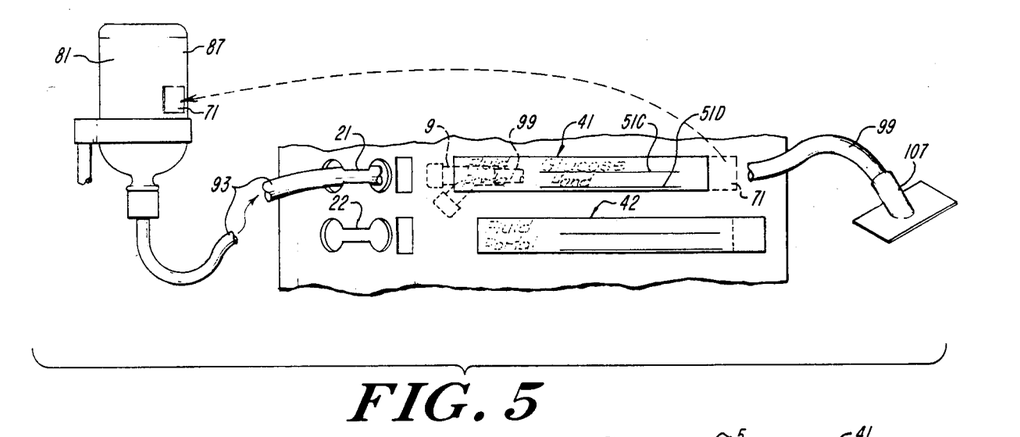
FIG. 5 is a partially exploded, fragmentary, partially enlarged, perspective view showing the steps of connecting a first tube in accordance with one modification of the present invention.
Figure 5A:
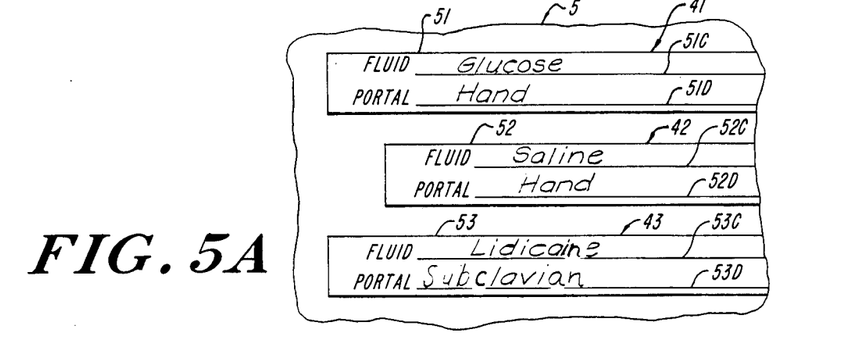
FIG. 5A is an enlarged fragmentary top plan view of another portion of the writing platform of FIG. 5 showing three tapes filled in to record the fluid and port for the first three tubes attached to the device.

Turning now to FIG. 5, as the first bottle is installed, such as bottle 87, the nurse locates the body port on the patient into which the fluid is to go, such as for example, the "hand" port 107, and traces this along the patient connecting tube 99 back to the Y connection 9 to which it is attached (or in some instances establishes such connection for the first time). She then places the bottle effluent tube 93 from the first bottle 87 in slot 21 which is the slot which has as its aligned tape the nearer tape of a pair, such as tape 41, and thus is the first slot of the slot pair 21-22 to receive a tube. Then the nurse fills in the blanks 51C and 51D, on tape 41 which pertain to the first bottle. As shown in FIG. 5A, she records the identification of the fluid in line 51C, which is a continuation of the legend "Fluid". For example, as shown at 51C in FIG. 5A, the nurse might write in the word "glucose". The nurse also fills in the line 51D which is a continuation of the legend: "Portal", to identify the port to which the line is connected. In the example, the nurse would write in the word, "hand", as shown at 51D in FIG. 5A. Then, as shown schematically in FIG. 5, the y connection 9 which she has previously located and been holding in her hand is connected to the already installed first effluent tube 93, and thus the Y connection 9 is automatically in alignment with the writing identifying the fluid flowing in the device, and , as a cross check, it is also in alignment with the identification of the port to which the patient connecting tube 99 is connected. At the same time, the handwritten entries automatically and accurately establish the accuracy of the color alignment means relative to the actual fluid flowing in the tube and the body portal to which it is directed. Finally, as a still further crosscheck, as shown in FIG. 5, the second color alignment tear tab, in this case, tab 71, having the same color as the body of the tape 41 is attached to the bottle, in this case, bottle 87, having the fluid 81 therein, which fluid has been identified as "Glucose" on the tape body 51. As a result of this procedure, not only has the careful selection of the proper port been enhanced by forcing the nurse to consciously enter the identification of the fluid and the name of the port to which she is making a connection, but even more important, the system is automatically in place to prevent confusion and error when a change is made in the tubing or flow connection through the Y connector 9 at a later date when there is a spaghetti like array of tubing in place. It should be noted that the color assistance provides for a complete system, and helps reinforce and expedite the visual alignment established by the present system. The present system makes accurate operation of a color aid possible, rather than visa versa.

Figure 6:
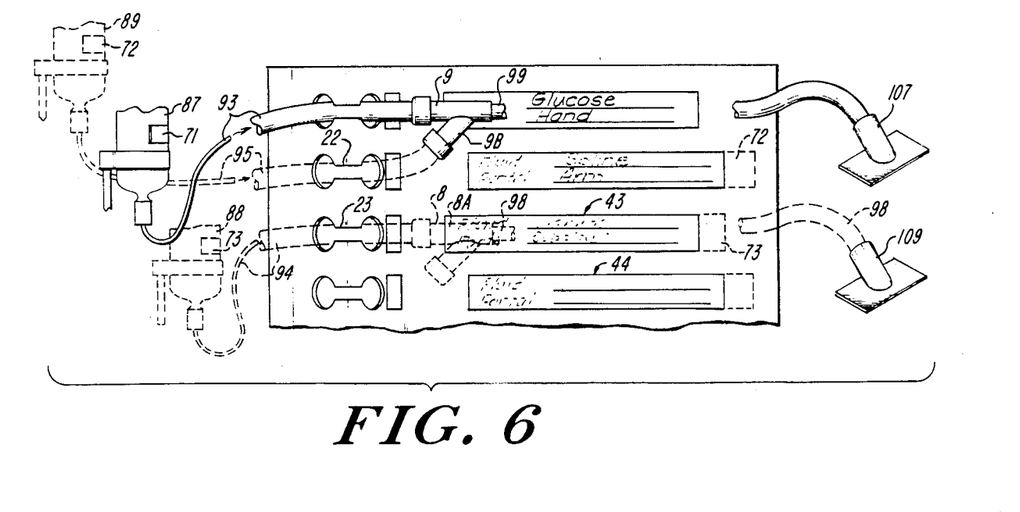
FIG. 6 is a partially exploded, fragmentary partially enlarged perspective view showing the steps of installing a second and third tube, with the third tube being installed to communicate with the same patient port as the first tube, in accordance with one modification of the invention.

Assume that the next fluid to be added is to go to a different body portal than the first fluid. Such procedure is shown in FIG. 6. In this case, the appropriate body portal such as clavical portal 109 would be located by the nurse who would then trace the line along the associated patient connecting tube 98 to its Y connector, in this case side port 8. The new tubing such as tube 94 from bottle 88 would be connected to the tube holding slot 23 in alignment with the nearer tape 43 of a new tape pair 43-44. The identification of the fluid and portal would be entered on the tape 43 in a manner similar to that described in connection with the installation of the first tube 93. For example, the fluid might be identified after the legend, "Fluid" as "Lidocaine" on line 53C of body 53 of tape 43. The side port branch 8A would then be connected to the newly connected bottle effluent tube 94, and the tab 73 would be attached to bottle 88 to complete the assembly.

Assume that a third bottle 89 is to be connected into the system, to provide a second fluid flowing into the hand portal 107. The nurse would read the writing platform 5 of the matrix device 10 to locate a tape having the word, "hand" thereon, in alignment with the word, "Portal", and having a y connector with an empty branch. In this case it would be the tape 41.(FIG. 6). As a cross check she would also read the aligned fluid identification, in this case, "Glucose", in the Fluid line, 51C to be sure there is compatability between such fluid and the fluid to be added, in the event there is to be a mixture of fluid flow through the y connector from both the old and new bottles. She would then follow substantially the same procedure as previously described in connection with making the first two installations. However, since the addition is to the second tape and second slot of a pair, she would place the tube 95 in slot 22 and add the fluid and portal information at 52C and 52D on tape 42, which is the tape which is further from the tube aligning means. For example, after placing the tube 95 in slot 22 and connecting the end of the tube to branch 9B of y connector 9, she would add the identification, of the new fluid, such as, for example, "saline", to the Fluid identification line 52C of tape body 52, and the identification, "Hand" to the portal identification line 52D of tape body 52 (FIGS. 5A and 6). Subconsciously she would reflect that because the new entry is on a tape which is further away from the tube holding means, it is the second of a pair to be added, and she would look again at the portal entry on both tapes of the pair to be sure they are identical, thus providing a further cross check. She would then complete the preferred method by removing the tear tab 72 and placing it on bottle 89. If she is conscientious, as she adds the tape to the bottle she would read the fluid indication on the bottle and quickly also read on the matrix the fluid identification to be sure it is the same. The color alignment which she has just established, together with the written notation, enables her to do this cross-check immediately and error free. By the foregoing arrangement, from the outset, the nurse is forced to consciously trace the tubing which enters and leaves the Y to determine the origin and insertion because she knows she must record the information to carry out the system. The necessity of following the process provides a conscious action which, by its very doing, reduces the chances of error, as compared to simply making tee connection and beginning to administer the fluid. In addition, the record is in place at the most likely source of error, the Y connection, so that when a future change is made in the fluid flowing through the Y to its connected port, a means is already in place to prevent the error of a misconection, despite the confusing spaghetti like array of tubing. Having followed the procedure of the invention, she can then open the stopcock and introduce the fluid into the system, with confidence that it is going to the correct port, and is compatable with the fluid with which it is being mixed, if that is what is occurring.

Moreover, the entire procedure can be done almost instantaneously, and actually faster than would be the case without the matrix device, with the accuracy assurance even greater enhanced. Because of the unique combination of hand, eye, writing, and color and spatial coordination, the entire operation can be handled with great speed and special accuracy.

Figure 7:
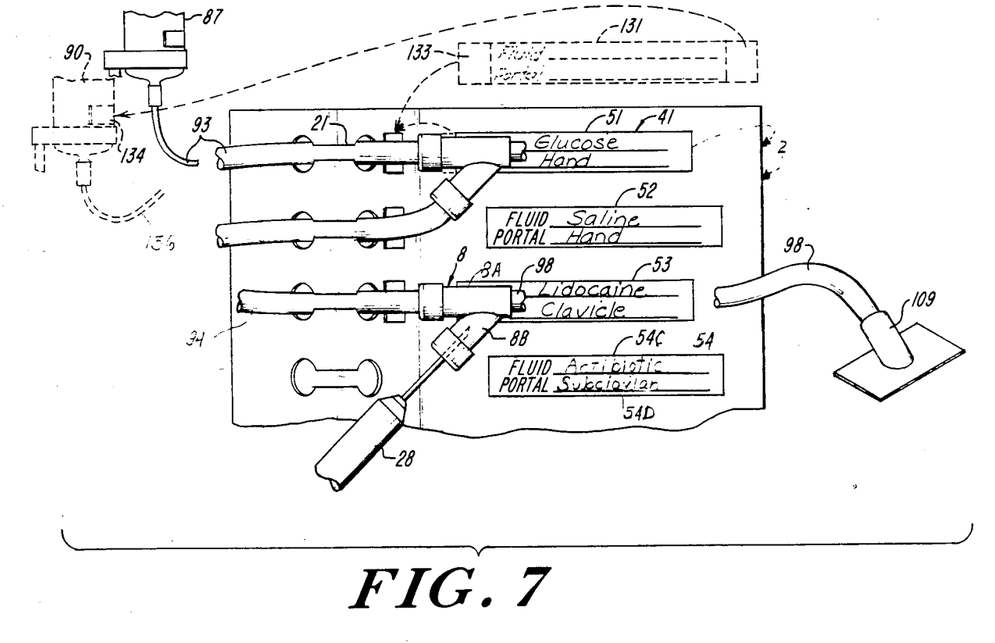
FIG. 7 is a partially exploded, fragmentary, partially enlarged perspective view showing the replacement of the first tube by another tube, and the first tape by another tape, and further showing the addition of fluids into the flow path of the second installed tube by use of an injection device, in accordance with one of the methods of the present invention.
Figure 7A:
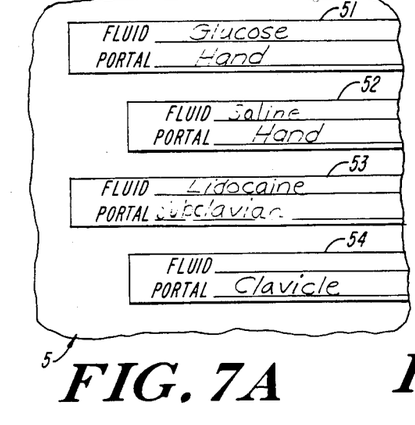

Assume, now, that instead of adding fluid by way of a bottle, it is necessary to add a medication by injection from a hypodermic needle, with the destination, for example, being the hand portal. Such injection by hypodermic needle occurs sometimes in an emergency when the correct port must be selected immediately. The nurse would scan the matrix looking for a side port, i.e. a rubber stoppered and unconnected branch of a y connection which is conventionally adapted to receive the point of a hypodermic needle through the rubber stopper. An example of such a condition is shown in FIG. 7 for branch 8B of side port 8. The nurse would read the tape opposite the connected branch 8A of the side port, in this case, tape 43, and see that it is connected to the subclavian, which is the proper portal for the fluid to be injected. She would also read the identification of the fluid already flowing in the tube to be sure that it is a fluid which can flow concurrently with the medicine being injected, and if not, if it is a fluid which can safely be cut off while the injection is occurring. The nurse would then turn to tape body 54 of tape 44 and fill in line 54C which is an extention of the legend "Fluid", with an identification of the fluid being inserted by the hypodermic needle, such as, for example, "Antibiotic". She would also fill in line 54D with an identification of the portal, in this case, "subclavian". She would then either make the injection immediately, or if applicable, shut off the flow in the already connected tube 94, and then make the injection. It is to be understood that if the emergency is too great she could first make the injection, and then record what she has injected on the tape body 54. What is important is that she has been able to instantaneously verify that she has access to the correct portal, and to know also inatantaneously what fluid is already flowing through the Y connection, before she makes the emergency injection.

Figure 7B:
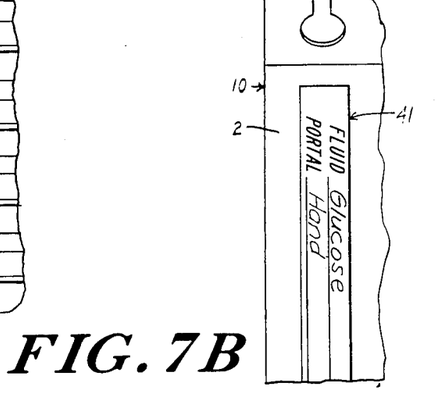
FIG. 7B is a fragmentary bottom plan view of the matrix device with the first recorded tape stored thereon.
Figure 7C:
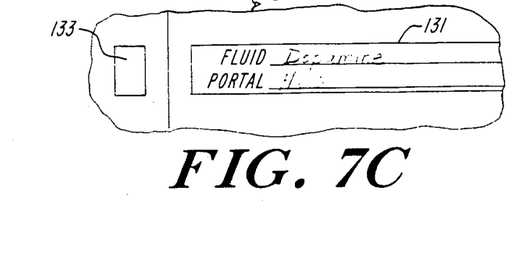
FIG. 7C is an enlarged fragmentary view of a portion of the writing platform with a replacement for the first tape in place and filled in to record the fluid and portal for the replacement bottle.

It is possible that over a period of time, so many changes are made in the medication supplied to a particular body portal that the appropriate spaces in the present device are used up. For example, a bottle, such as bottle 87 may be temporarily or permanently disconnected from the system, and a new bottle, such as bottle 90 containing Dopamine to be added. The present device and system can provide for such event by the use of additional or auxilliary colored tape which comes on a separate roll. The nurse merely reads the existing tape body 51 (FIG. 7) to be sure that the portal is the portal to which the substitute bottle is to be connected, disconnects the tubing 93 (FIG. 7) for the old bottle 87, removes the tape 41 which recorded the fluid and portal for bottle 87, and affixes it to the bottom of the matrix 10 for permanent record, as shown in FIGS. 7 and 7B. She then places a new tape 131 in place of the old tape, and records the fluid and portal in the same manner as previously described. She then removes the colored tab 133 which corresponds to the color of the new tape 131, if it is not the same color as the old tape, and places it below the slot 21, either covering the old tab, or after removing and discarding the old tab. As a cross check, she also places the colored tear tab 134 on bottle 90, and reads the fluid both on the bottle and on the matrix tape 131 to be certain they are the same. She then renders the newly added tube operative, such as by opening a stopcock.

It is apparent that an added advantage of the foregoing device is that a complete record keeping system is automatically provided in carrying out the operational error prevention aspect of the system. Such automatic record keeping is very beneficial due to the increased emphasis in hospitals in record keeping, both as a method of increasing the quality of patient care and as proof in the event of malpractice litigation. Not only is this valuable for future evidence, but it would also be helpful in routine checks by a supervisor who could compare the bedside chart to the matrix device to see if they are identical, and if not, to take immediate steps to determine whether an error has been made in the entry in the bedside chart.

Figure 8:
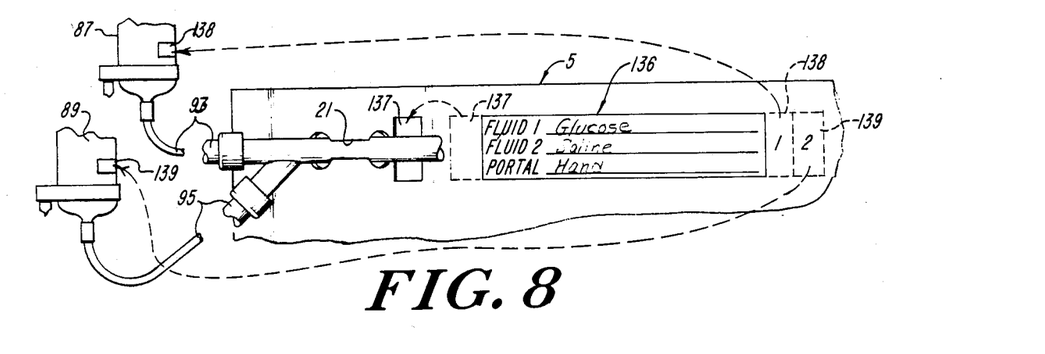
FIG. 8 is a partially schematic fragmentary, partially enlarged perspective view showing a modification wherein a patient connector tube rather than a bottle effluent tube is installed in a holding means of the matrix.
Figure 8A:
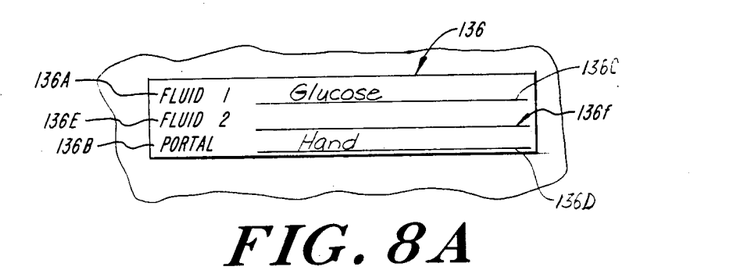
FIG. 8A is an enlarged, fragmentary, top plan view of a portion of the writing platform of FIG. 8 showing a tape filled in to record two fluids on one tape in accordance with the modification.

While the foregoing arrangement wherein the matrix device is installed above the Y connections is preferred, the system may also be used, but with a lesser degree of certainty when the device is installed below the Y connection, i.e. between such connection and the body port. In this arrangement, the staggering of the tapes would have no significance. In making the connection of a new tube to the y connector the nurse would be able to readily determine the port involved by reading the tape alignet with the slot holding the patient connecting tube. In this modification, an additional means of recording a fluid would be provided. As shown in FIGS. 8 and 8A, the tape 136 would have an additional line, bearing the legend, "Fluid No. 2" as shown at 136E. When a second connection is made to the same portal, the new fluid would be identified in line 136F, which is a continuation of the legend, "Fluid No. 2". Of course, the legend of Line No. 136A would then be "Fluid No. 1", and the legend of line 136B would be "Portal", as shown. In addition, the tape 136 would have a first tab 138 to place on bottle 87 from which tube 93 emits, and a second tab 139 to place on bottle 89 from which tube 95 emits. It would also have a colored tab 137 to place below the appropriate slot, such as 21. FIG. 8A shows a sample filled in.

Figure 9:
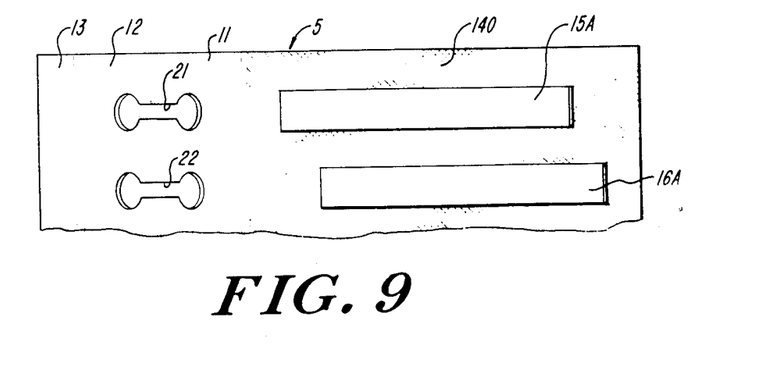
FIG. 9 is a fragmentary perspective view of the recording means with a modified guide means.

It is to be understood that rather than recesses other guide means could facilitate the alignment of the recording of the fluid and portal. For example, as shown in FIG. 9, if it is desired to write directly on the recording platform, the platform could be textured, as at 140, but having for the guide means smooth portions on which the entries could be made, as shown at 15A and 16A in FIG. 9.

While this invention has been described with respect to specific embodiments thereof, it should be understood that not all the aspects of the preferred embodiments need necessarily be used, but an elimination of some aspects of the embodiments would result in a corresponding reduction of at least same of the advantages associated therewith. Similarly it should also be understood that this invention is not limited to these embodiments and that the appended claims are intended to include these and other features and embodiments as may be devised by those skilled in the art which are nevertheless within the spirit and scope of this invention.

I claim:

1. A device for controlling the administration of intravenous fluids comprising:
   a matrix member,
   a plurality of spaced tube aligning means on said matrix member for orienting a plurality of intravenous fluid tubes in a particular spaced alignment relative to said matrix member
   recording means positioned on said matrix member relative to said tube aligning means to provide for the handwritten recording of data relative to said tubes in visual alignment with said tube aligning means whereby said data in correlation with the tube positions facilitates the determination of the accuracy of injection of new intravenous fluids into an existing line of flow.

2. A device in accordance with claim 1 wherein said recording means has guide means for guiding said visual alignment between the handwritten recording and the aligned tubing.

3. A device in accordance with claim 2 wherein said guide means includes tape means.

4. A device in accordance with claim 3 where said tape means is replaceable.

5. A device in accordance with claim 2 wherein said guide means has a pair identification means.

6. A device in accordance with claim 5 wherein said pair identification means comprises staggered tapes.

7. A device in accordance with claim 1 wherein said spaced tube aligning means has pair identification means.

8. A device in accordance with claim 7 wherein said pair identification means comprises webs of staggered heights.

9. A device in accordance with claim 5 wherein said pair identification means includes color coding.

10. A device in accordance with claim 7 wherein said pair identification means includes color coding.

11. A device in accordance with claim 4 wherein said matrix member has storage means for storing the replaced tape.

12. A device in accordance with claim 3 including indicia means detachably mounted on said tape means in visual alignment with said tube aligning means and having adhesive means for applying said indicia means to an IV fluid container to provide a correlation between said container and information recorded in writing on said recording means.

13. A device in accordance with claim 3 wherein each said tape means has a color code, and wherein the same color is disposed on said tube aligning means in visual alignment between a portion of said tube aligning means and said tape means.

14. A device in accordance with claim 1 wherein said recording means includes portal identification means in visual alignment with said tube aligning means for the addition of the identification of a port on the body of a patient to which tubing in alignment with the identification of the port is connected.

15. A device in accordance with claim 1 wherein said recording means includes fluid identification means in visual alignment with said tube aligning means for the addition of the identification of fluid flowing in the tubing in alignment with said prerecorded fluid identification means.

16. A device in accordance with claim 15 including at least one additional prerecorded fluid identification means in visual alignment with said tube aligning means for the addition of the identification of another fluid flowing in the tubing in alignment with the tube aligning means.

17. A device in accordance with claim 1 wherein said recording means comprises a platform of at least two inches length.

18. A method of controlling the administration of intravenous fluid in a plurality of tubes which have flow juncture means disposed between the fluid containers and the entrance ports on a patient comprising:
   Placing a matrix device on a plurality of tubes adjacent the flow juncture means whereby the tubes are aligned in spaced disposition relative to said matrix device and wherein the matrix device includes means for written recording of data relating to the fluid flowing in the tubing which is in visually spaced alignment with the written data, Recording information about the fluid flowing through each tubing in visual alignment with the recording to facilitate the determination of the accuracy of injection of new intravenous fluids into the existing line of flow.

19. A method in accordance with claim 18, wherein the information recorded includes the portal to which the fluid flowing in said visual alignment is connected.

* * * * *